(12) United States Patent  (10) Patent No.: US 8,501,111 B2
Xu  (45) Date of Patent: Aug. 6, 2013

(54) SMALL VOLUME AND FAST ACTING OPTICAL ANALYTE SENSOR

(76) Inventor: Tom Cheng Xu, Castro Valley, CA (US)

( * ) Notice: Subject to any disclaimer, the term of this patent is extended or adjusted under 35 U.S.C. 154(b) by 0 days.

(21) Appl. No.: 13/447,165

(22) Filed: Apr. 14, 2012

(65) Prior Publication Data

US 2013/0102065 A1  Apr. 25, 2013

Related U.S. Application Data

(63) Continuation-in-part of application No. 12/454,639, filed on May 21, 2009, now abandoned.

(51) Int. Cl.
*G01N 1/00* (2006.01)
(52) U.S. Cl.
USPC ........... 422/412; 422/400; 422/401; 422/408; 422/68.1
(58) Field of Classification Search
USPC ................... 422/57, 400, 401, 408, 412, 68.1
See application file for complete search history.

(56) References Cited

U.S. PATENT DOCUMENTS

| | | |
|---|---|---|
| 4,396,714 A | 8/1983 | Maeda |
| 4,935,346 A | 6/1990 | Philips |
| 5,049,487 A | 9/1991 | Philips |
| 5,059,394 A | 10/1991 | Philips |
| 5,179,005 A | 1/1993 | Philips |
| 5,296,192 A | 3/1994 | Carroll |
| 5,304,468 A | 4/1994 | Philips |
| 5,453,360 A | 9/1995 | Yu |
| 5,859,937 A | 1/1999 | Nomura |
| 5,972,294 A | 10/1999 | Smith |
| 6,040,195 A | 3/2000 | Carroll |
| 6,099,484 A | 8/2000 | Douglas |
| 6,157,442 A | 12/2000 | Raskas |
| 6,551,494 B1 | 4/2003 | Heller |
| 6,924,093 B2 | 8/2005 | Haviland |
| 2003/0077205 A1 | 4/2003 | Xu |
| 2009/0221101 A1 * | 9/2009 | Jerome et al. ................. 436/518 |
| 2010/0297601 A1 | 11/2010 | Xu |

* cited by examiner

*Primary Examiner* — Monique Cole

(57) ABSTRACT

A fast acting sensor designed to accommodate an aqueous analyte-containing sample having a volume of less than one microliter and that can be used to quantify the amount and concentration of such analyte in the sample through light reflectance or fiber-optic light reflectance. The sensor includes a storage chamber, a capillary passage, and a reaction membrane. The storage chamber acts to collect the sample and to secure such sample while it undergoes detection. The capillary passage acts to direct the sample over the reaction membrane and controls the diffusion of the sample in the storage chamber. The reaction membrane contains all of the chemicals and enzymes needed to cause a color-change reaction when contacted with the sample. The amount of analyte can be determined by light reflectance intensity with an optical measurement instrument.

8 Claims, 4 Drawing Sheets

SMALL VOLUME AND FAST ACTING OPTICAL ANALYTE SENSOR

CROSS-REFERENCE TO RELATED APPLICATIONS

This application is a continuation-in-part of U.S. application Ser. No. 12/454,639 filed on May 21, 2009, titled "SMALL VOLUME AND ULTRA SPEED COLORIMETRIC SENSOR," which is entirely incorporated herein by reference in its entirety and made a part of this specification for all that it discloses.

BACKGROUND OF THE INVENTION

1. Field of the Invention

The present invention relates to optical analyte sensors; more specifically, to sensors configured to accommodate submicroliter liquid sample volumes in the rapid detection of analytes in such samples.

2. Description of the Prior Art

Portable analyte monitoring devices, such as portable blood glucose monitors, typically require sensors for the quantification of analytes in biological samples. These sensors are designed to receive fluid samples from their users and are oftentimes discarded after each use. The frequent purchase and use of such sensors has become an indispensible part of the lives of many diabetics. Individuals with Type 1 diabetes are often advised to measure their blood glucose levels three or more times per day. However, the pain associated with blood sample collection and the frequency of such measurements, which necessitate the purchase of numerous sensors, cause many diabetics to falter from their suggested monitoring schedules. The prior art has sought to remedy these complications by operating on less blood from their users and favoring design features that lower the cost of such sensors. Features that lead to more rapid test results can also result in more frequent self-monitoring.

U.S. Pat. Nos. 4,935,346, 5,049,487, 5,059,394, 5,179,005 and 5,304,468 to Phillips et al. discloses various methods and devices for applying a sample of whole blood to the "sample" side of a sensor membrane that is impregnated with the necessary reagents. Red blood cells are then separated by this membrane as the remaining sample migrates toward the "testing" side of the membrane. The glucose in the remaining sample then interacts with the reagents to produce a light-absorbing reaction product. An optical measurement instrument can then be used to measure the color change which correlates to the blood glucose level in the sample. U.S. Pat. No. 5,972,294 to Smith et al. discloses a reagent sensor dependent on a membrane for receiving a fluid sample and separating red blood cells from such a sample before an assay is performed. U.S. Pat. Nos. 5,296,192 and 6,040,195 to Carroll et al. describe an improved multi-layered sensor for receiving a whole blood sample. The sensor includes filtration layers to remove red blood cells, fluid volume control dams to prevent spillage of the fluid from the sensor, and a chemical reagent formulation that facilitates end-point testing. U.S. Pat. No. 6,924,093 to Haviland et al. discloses an alignment notch added to a sensor and an obround-shaped aperture for receiving fluid samples. Both features are intended to reduce the amount of a fluid sample needed to provide an assay. Haviland indicates that the purpose of the alignment notch is to facilitate proper alignment of the sensor within a measuring instrument such that the sample-receiving aperture is accurately aligned over the instrument's light source. Prior to such an improvement, sensors compensated for the likelihood of misalignment by providing a larger measurement area in the form of a larger aperture. Such an aperture naturally required a greater sample volume to saturate.

While the aforementioned sensors are all widely used, they share some common limitations. First, since blood from a diabetic patient must be applied to either a top "sample" layer or a top-facing aperture of the aforementioned sensors, 3 μL to 50 μL of blood must be obtained from a patient using such a sensor. A patient must often obtain any sample volume larger than 3 μL by lancing the skin on his or her fingertips and, subsequently, milking the area to obtain a useful sample volume. This procedure is a nuisance for the patient and is often painful. Less painful methods for obtaining a sample include lancing the arm or thigh, both of which have a lower nerve ending density than fingertips. However, lancing the body in such regions often produces inadequate sample volumes because these regions are not heavily inundated with the necessary blood vessels. In addition, most current sensors are not designed to accept blood from these regions of the body due to the restricted accessibility of these regions of the body to the sample area on the sensor. Although U.S. Pat. No. 6,099,484 to Douglas et al. has aimed to solve this problem by using a capillary device as a wick to transfer fluid samples to the sensor pad, adding the capillary device disclosed by Douglas to most sensors would be impractical and increase the cost of such sensors prohibitively.

Moreover, since the analyte of interest is often measured by a light signal reflected off the surface of a sensor where a color reaction has taken place, the sensor has to be inserted into an optical measurement instrument's protective shroud during testing to avoid interference from environmental or ambient light. This also requires that the surface of the sensor be closely placed near the light source and the light detector of the instrument. Repeated testing could potentially result in contamination of the instrument by blood or other biological fluids and lead to inaccurate test results.

Finally, another desired feature for a self-monitoring system is to obtain the results of such measurements rapidly, for example, in less than three seconds. Diabetic patients normally measure their glucose levels before each meal. Obtaining the results of such measurements rapidly is always desired, especially for patients who are children.

To overcome these limitations, it is desirable to develop a sensor that requires minimal sample volume, reduces contamination to measurement instruments, exhibits a measurable change in optical properties rapidly, and is capable of using not only blood samples from fingertips but also blood samples from other parts of the body, such as the arm and thigh, which have lower nerve ending densities making the sampling process less painful or even painless. Over the past two decades, a wide variety of optical sensors have been proposed for analysis of chemical species in industrial, environmental and biological samples. These sensors operate by detecting optical changes of a sensing material or indicator dye on interaction with an analyte. Due to the variety of analyte-specific indicators available, such sensors may be used for monitoring a large number of analytes, including blood glucose levels for patients with diabetes.

For example, U.S. Pat. No. 5,859,937 to Nomura disclosed a sensor comprising an atomic oxygen etched optical fiber with analyte-responsive reagents deposited on the etched surface. The analyte concentration was measured by physical or chemical response upon being contacted with the reagents. However, optical fiber surface etching described in the patent is not practical for making reproducible and reliable sensors. Raskas in U.S. Pat. No. 6,157,442 described a micro optical fiber sensor device, but it is only for in vivo use.

The current invention discloses a novel reflectance optical sensor that utilizes submicroliter sample volumes for analyte detection and quantitative determination within three seconds of time. The new invention also discloses a sample collecting storage chamber and capillary passage which improve the accuracy and reliability of such measurements when used with standard optical measurement instruments.

SUMMARY OF THE INVENTION

The illustrated embodiments of the present invention are directed to a fast acting optical sensor that can be used for the detection and quantification of analytes in small volume aqueous samples. The sensor comprises a base support member, a reaction membrane, a storage chamber, and an open-ended capillary passage for conducting said sample from an incision into said storage chamber for reaction with the reaction membrane and detection by an optical measurement instrument. The present invention may utilize a number of enzymatically-mediated colorimetric reactions and is particularly suitable for use with an optical measurement instrument comprised of a light source and a light sensor.

One embodiment of the invention is configured for determining the concentration of an analyte in an aqueous sample by contacting the sample with the open-ended capillary passage. The capillary passage conducts the sample into the storage chamber for sample storage and reaction with the reaction membrane. In this embodiment, the reaction membrane is coated with coloring chemicals and enzymes. Upon reaction with the reaction membrane, a colored product is produced which can then be detected by an optical measurement instrument comprising a light source and a light sensor.

These and other features of the invention will become apparent to those skilled in the art upon reviewing the drawings and accompanying descriptions of the current invention presented below.

DETAILED DESCRIPTION OF THE PREFERRED EMBODIMENT

Figure 1:
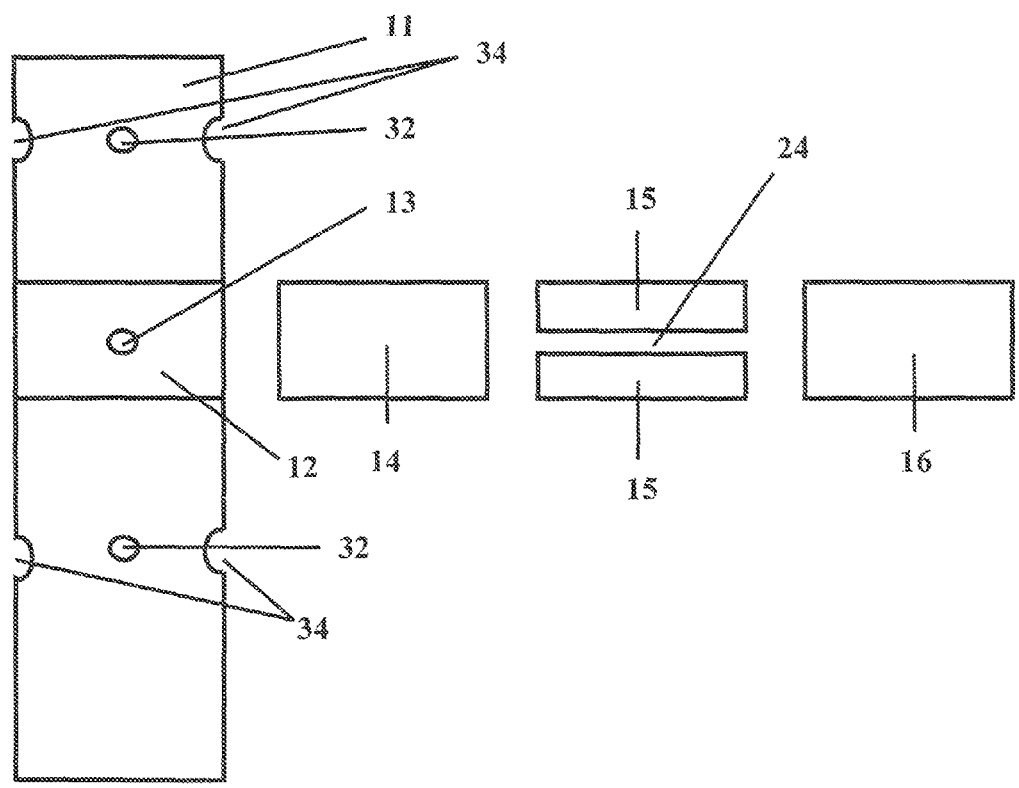
FIG. 1 shows an exploded schematic top view of one embodiment of the sensor in accordance with the principles of the present invention.

Unless otherwise indicated, all technical and scientific terms used herein have the same meaning as commonly understood by one of ordinary skill in the art. It is acknowledged that this invention is not limited to any particular embodiments described and that any embodiments similar or equivalent to those described herein can also be used in the practice or testing of the present invention.

Disclosed herein is a sensor designed to receive and store an aqueous sample from a user having a volume less than about 1 microliter, preferably less than about 0.5 microliter, more preferably less than about 0.3 microliter, and most preferably less than about 0.1 microliter. Upon interaction with analytes in the sample, the sensor will produce a color change that can be measured with an optical measurement instrument within 10 seconds of time, preferably within 5 seconds, and more preferably within 3 seconds of time. The sample of interest is typically a biological fluid, such as blood or serum, and the analyte of interest is typically glucose, cholesterol, or triglycerides. The present invention does not require the use of electrodes or reduction-oxidation (or redox) mediators. As depicted in the drawings in general and FIGS. 3 and 4 in particular, the sensor comprises a plastic base support member 11, a reaction membrane 14, and a storage chamber 30 comprising an open-ended capillary passage 24 for conducting the analyte sample from an incision laterally across the width of the storage chamber and simultaneously permitting the sample to saturate reaction membrane 14 without the aid of an additional sorbent material. Reaction membrane 14 does not require the use of redox mediators to effect a color change. Also, storage chamber 30 is constructed on only one side of the membrane so that the opposite side is used for color detection by an optical measurement instrument.

Base Support Member

The small volume and fast acting sensor of the present invention is constructed according to FIG. 1. Base support member 11 provides support for said sensor and can be constructed of any inert material, examples of which include polystyrene, polypropylene, and polytetrafluoroethylene. Base support member 11 is laminated with a double-sided adhesive 12. An aperture 13 is bored through on the base support member 11. Reaction membrane 14 is laminated directly onto base support member 11 by adhesive 12. Inert and non-conductive circular cutouts 32 and half-circular cutouts 34 are also made directly on base support member 11 as means for the sensor to engage with an optical measurement instrument from either the right or left side of the sensor. These circular cutouts 32 are bores with a surface area no greater than 1 mm$^2$. The half-circular cutouts are half-circle bores located at the edges of the base support member 11. The location of such circular and half-circular cutouts allows the sensor to be used with ease by either a left-handed or right-handed patient. Upon engagement of the sensor with an optical measurement instrument, aperture 13 allows a portion of the reaction membrane 14 to be exposed to the optical measurement instrument.

Storage Chamber and Capillary Passage

Figure 2:
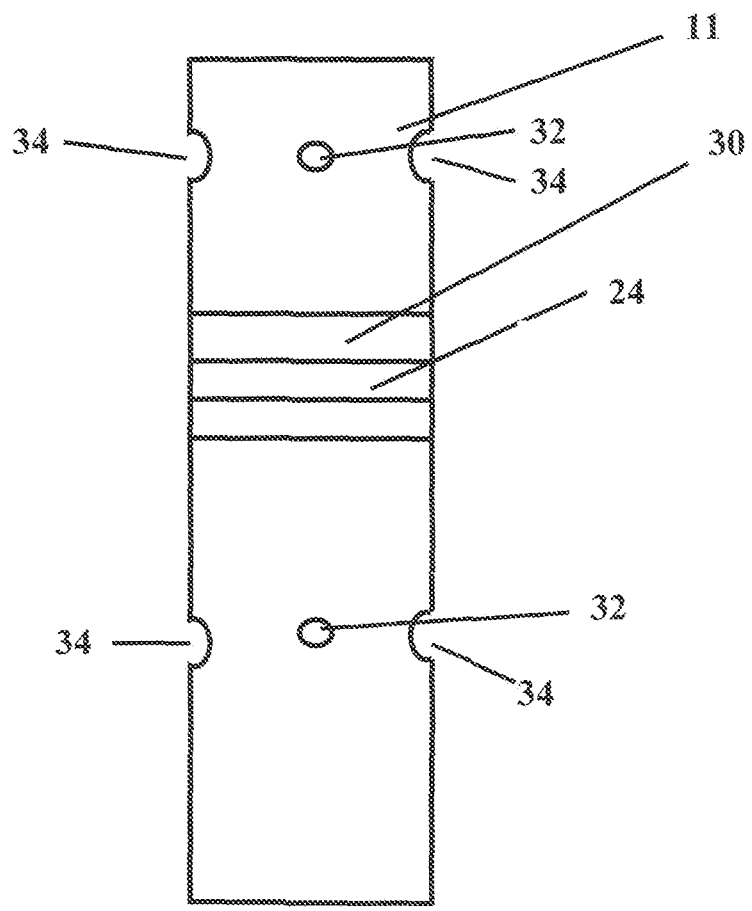
FIG. 2 shows a schematic top view of the assembled sensor of FIG. 1 in accordance with the principles of the present invention.
Figure 3:
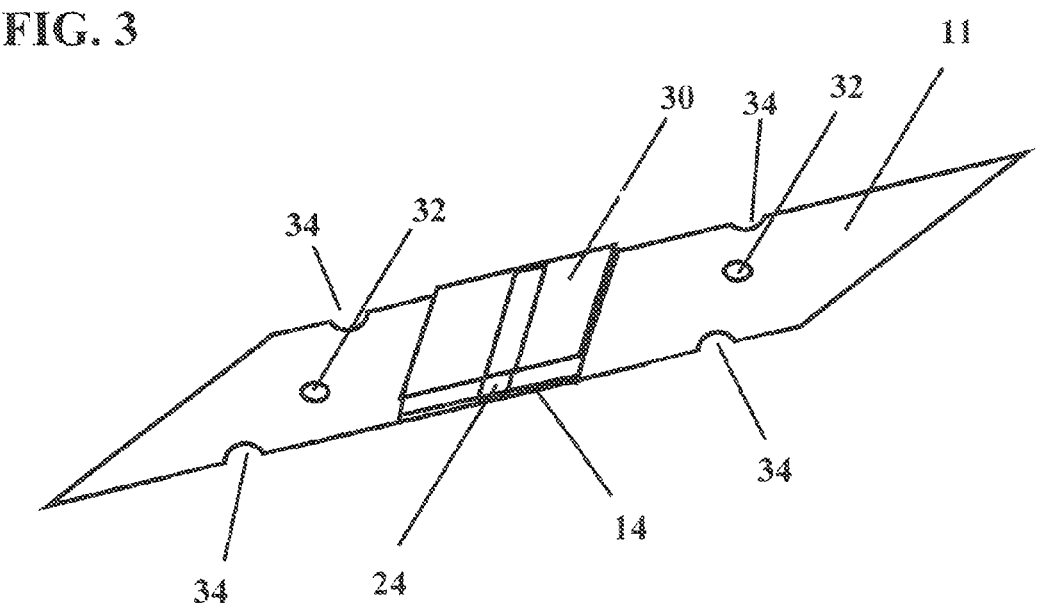
FIG. 3 shows a perspective top view of one embodiment of the assembled sensor of FIG. 1.
Figure 4:
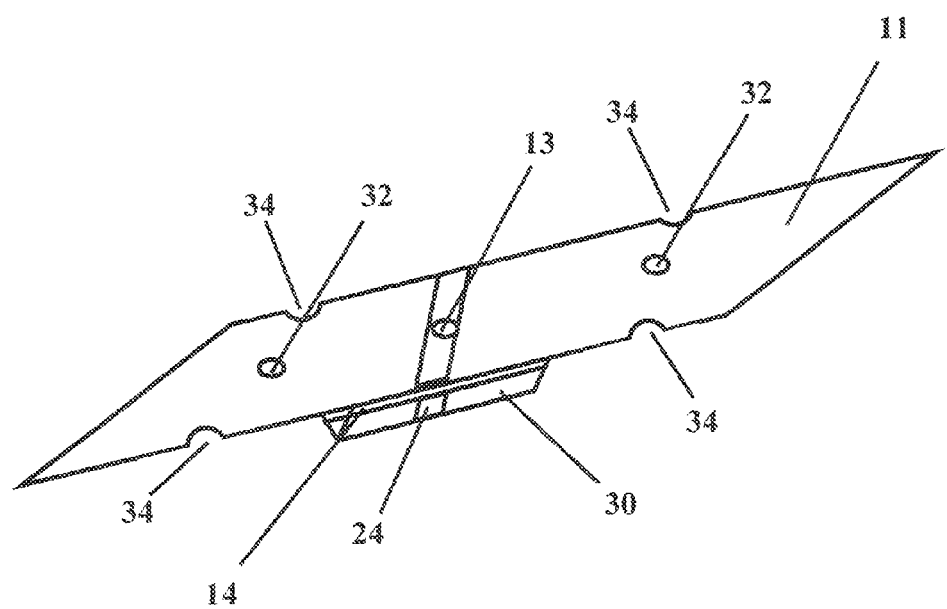
FIG. 4 shows a perspective ventral view of one embodiment of the assembled sensor of FIG. 1.

As depicted in FIG. 1, two chamber supports 15 are laminated approximately 0.5 mm apart and directly onto reaction membrane 14 by a double-sided adhesive. The two chamber supports 15 can be constructed of any material that possesses capillary properties. As shown in FIG. 1, the two chamber supports 15 are covered by membrane cover 16 to create a storage chamber 30, as shown in FIGS. 3 and 4, comprising an open-ended capillary passage 24 positioned directly over reaction membrane 14. Membrane cover 16 can be constructed of a transparent material to allow the user to view the saturation of reaction membrane 14 occurring inside storage chamber 30. As depicted in FIGS. 2, 3, and 4, the open ends of capillary passage 24 extend to the lateral edges of base support member 11 and permit the saturation of reaction membrane 14 without an additional sorbent material. The open ends of the capillary passage 24 prevent uncontrolled diffusion of the analyte sample throughout storage chamber 30.

FIG. 2 shows an example of an assembled sensor comprising storage chamber 30 and capillary passage 24. FIG. 3 shows a perspective top view of one embodiment of the assembled sensor with the position of reaction membrane 14 relative to storage chamber 30 clearly labeled. FIG. 4 shows a perspective ventral view of one embodiment of the assembled sensor with the position of aperture 13 relative to capillary passage 24 clearly depicted. FIG. 4 shows that capillary passage 24 is configured to align the analyte sample over an area of reaction membrane 14 in vertical alignment with aperture 13. Also, as can be seen in FIGS. 1 and 4, the ventral side of capillary passage 24 is exposed directly to reaction membrane 14 and the width of capillary passage 24 is no greater than the diameter of aperture 13.

Reaction Membrane

The reaction membrane 14 is a uniformly porous membrane impregnated with such chemicals and enzymes as required by the assay of the interested analyte. A hydrophilic membrane comprising of any of nylon, polyester or polysulfone can be used for reaction membrane 14. To prepare the membrane, a signal producing reagent solution is first formulated. The membrane is impregnated by this solution by submersing the membrane in the solution and then dried. Various signal generating solutions can be used to impregnate the membrane and no redox mediators are incorporated into the membrane.

When oxidase/peroxidase enzymes are utilized, the following signal producing chemicals or chemical pairs can be used: 3-methyl-2-benzothiazolinone hydrazone (MBTH) and 3-dimethylaminobenzoic acid (DMAB), as described in U.S. Pat. No. 5,049,487 Phillips et al., (MBTH) and 8-anilino-1-naphthalenessulfonate (ANS), as described in U.S. Pat. No. 5,453,360 Yu, MBTH and 3-dimethylaminobenzoic acid (DMAB), as described in U.S. Pat. No. 5,049,487 Phillips et al., sulfonated-MBTH and N-(3-sulfopropyl)aniline (HALPS), as described in U.S. Pat. No. 4,396,714 Maeda et al. An example of such a test using N-ethyl-N-(2-hydroxy-3-sulfopropyl)-3,5-dimethylaniline (MAOS) and 4-Aminoantipyrine is disclosed in U.S. Pat. No. 6,040,195 to Carroll et al.

Example

The following example is used to further characterize the invention and not meant to limit the scope of the invention. Variations within the concepts of the invention are apparent to those skilled in the art.

Construction of Storage Chamber and Capillary Passage

A small volume and fast acting sensor of the present invention was constructed according to one embodiment of the invention depicted in FIGS. 1, 2, 3, and 4. A polystyrene strip of 0.13 mm thickness was used to make base support member 11. Base support member 11 was then laminated with a double-sided adhesive 12 of 0.1 mm thickness. An aperture 13 with a surface area no greater than approximately 1.0 $mm^2$ was bored directly on the adhesive-laminated base support member 11. The aperture 13 was then covered completely with reaction membrane 14. Two chamber supports 15 of 0.1 mm were laminated approximately 0.5 mm apart and directly onto reaction membrane 14 by a double-sided adhesive. The two chamber supports 15 were then covered by a transparent membrane cover 16 to create a storage chamber 30 comprising an open-ended capillary passage 24 positioned directly over reaction membrane 14. The open ends of capillary passage 24 extend to the lateral edges of base support member 11 and permit the saturation of reaction membrane 14 without an additional sorbent material. The open ends of the capillary passage 24 prevent uncontrolled diffusion of the analyte sample throughout storage chamber 30.

Preparation of Reaction Membrane

A reaction membrane was prepared by first formulating a signaling solution containing 40 mg of MBTH, 80 mg of DMAB, 10 mg of EDTA disodium salt, 0.668 g of sodium citrate, 0.523 g of citric acid, 3000 units of horseradish peroxidase, 4500 units of glucose oxidase, 100 mg of BSA, and 100 mg of PVP-360K in 10 ml of deionized $H_2O$. A piece of Pall Supor® membrane, 0.8 micron thick, was then coated with the solution. After blotting off excess signaling solution, the reaction membrane was dried by forced airflow at room temperature.

While the invention has been described with reference to specific embodiments, modifications and variations of the invention may be constructed without departing from the scope of the invention.

What is claimed is:

1. A sensor for receiving, storing, and chemically reacting with fluid samples from a user for purposes of detecting and quantifying the amount of analytes in such samples by optical means using an optical measurement instrument, such a sensor comprising:

a base support member, such a base support member providing support for said sensor and having an aperture that allows a portion of a reaction membrane to be exposed to said optical measurement instrument;

said reaction membrane having a surface which is in physical contact with said base support member and covers all of said aperture, said reaction membrane comprising at least one reagent for reacting with at least one compositional component of said analytes and requiring no redox mediators for reaction;

a storage chamber comprising an open-ended capillary passage for conducting said sample from an incision laterally across the width of said storage chamber and simultaneously permitting said sample to saturate said reaction membrane without an additional sorbent material, wherein:

said storage chamber is attached directly to said base support member and said open-ended capillary passage is positioned directly over said reaction membrane;

the open ends of said capillary passage extends to the lateral edges of said base support member and permits saturation of said reaction membrane without an additional sorbent material;

the ventral side of said capillary passage is exposed entirely to said reaction membrane and the width of said capillary passage is no greater than the diameter of said aperture;

said capillary passage is configured to align said sample over an area of said reaction membrane in vertical alignment with said aperture; and said capillary passage is sized to contain a volume of less than about 1 µL of said sample and where the open ends of said capillary passage prevents uncontrolled diffusion of said sample into said storage chamber; and whereby said sensor is used to measure the amount of analytes in such fluid samples without the use of electrodes on said sensor.

2. The sensor of claim 1, wherein said capillary passage is sized to contain a volume of less than about 0.5 µL of said sample and where the open ends of said capillary passage prevents uncontrolled diffusion of said sample into said storage chamber.

3. The sensor of claim 1, wherein said capillary passage is sized to contain a volume of less than about 0.1 µL of said sample and where the open ends of said capillary passage prevents uncontrolled diffusion of said sample into said storage chamber.

4. The sensor of claim 1, wherein said aperture has a surface area no greater than approximately 1.0 mm$^2$.

5. The sensor of claim 1, wherein said base support member comprises multiple inert and non-conductive circular and half-circular cutouts made directly on said base support member as means for engagement with said optical measurement instrument from either the right or left side of said sensor.

6. The sensor of claim 5, wherein said multiple cutouts are circular bores with a surface area no greater than 1 mm$^2$ and said multiple half-circular cutouts are half-circular bores located at the edges of said base support member as means for engagement with said optical measurement instrument.

7. The sensor of claim 1, wherein the top of said storage chamber is comprised of a transparent material for ease of viewing by said user.

8. The sensor of claim 1, wherein said reaction membrane comprises a hydrophilic material.

* * * * *